United States Patent
Keimel

(10) Patent No.: US 6,666,821 B2
(45) Date of Patent: Dec. 23, 2003

(54) SENSOR SYSTEM

(75) Inventor: John G. Keimel, North Oaks, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 10/040,827

(22) Filed: Jan. 8, 2002

(65) Prior Publication Data

US 2002/0120186 A1 Aug. 29, 2002

Related U.S. Application Data

(60) Provisional application No. 60/260,237, filed on Jan. 8, 2001.

(51) Int. Cl.[7] .............................. A61B 5/05; A61B 5/00
(52) U.S. Cl. ........................ 600/365; 600/345; 600/347; 600/372; 600/373; 600/377
(58) Field of Search ................................ 600/365, 345, 600/347, 364, 366, 372, 373, 374, 375, 376, 377, 378, 379, 380, 381, 395, 396, 397, 300, 309

(56) References Cited

U.S. PATENT DOCUMENTS

| | | | | |
|---|---|---|---|---|
| 4,534,825 A | * | 8/1985 | Koning et al. | 600/348 |
| 4,757,022 A | | 7/1988 | Shults et al. | 435/291 |
| 4,991,582 A | | 2/1991 | Byers et al. | 128/419 P |
| 4,994,167 A | | 2/1991 | Shults et al. | 204/403 |
| 5,390,671 A | | 2/1995 | Lord et al. | 128/635 |
| 5,391,250 A | | 2/1995 | Cheney II, et al. | 156/268 |
| 5,482,473 A | | 1/1996 | Lord et al. | 439/67 |
| 5,586,553 A | | 12/1996 | Halili et al. | 128/635 |
| 5,750,926 A | | 5/1998 | Schulman et al. | 174/52.3 |
| 5,782,891 A | | 7/1998 | Hassler et al. | 607/36 |
| 5,797,898 A | | 8/1998 | Santini, Jr. et al. | 604/890.1 |
| 5,820,589 A | | 10/1998 | Torgerson et al. | 604/93 |
| 5,999,848 A | | 12/1999 | Gord et al. | 607/2 |
| 6,001,067 A | | 12/1999 | Shults et al. | 600/584 |
| 6,169,925 B1 | | 1/2001 | Villaseca et al. | 607/60 |
| 6,203,758 B1 | * | 3/2001 | Marks et al. | 422/68.1 |
| 6,248,080 B1 | | 6/2001 | Miesel et al. | 600/561 |
| 6,331,163 B1 | * | 12/2001 | Kaplan | 600/486 |

OTHER PUBLICATIONS

Koudelka–Hep, "Electrochemical Sensors for in vivo Glucose Sensing", *Biosensors in the Body: Continuous in vivo Monitoring*, John Wiley & Sons, p. 57–77, 1997.

Updike et al., "Principles of Long–term Fully Implanted Sensors with Emphasis on Radiotelemetric Monitoring of Blood Glucose from inside a Subcutaneous Foreign Body Capsule (FBC)", *Biosensors in the Body: Continuous in vivo Monitoring*, John Wiley & Sons, p. 117–137, 1997.

Bae et al., "Pulsatile Drug Release by Electric Stimulus", ACS Symposium Series, 1994, 545, pp. 98–110.

Kwon et al., "Electrically Erodible Polymer Gel for Controlled Release of Drugs", Nature, 1991, 354, pp. 291–293.

Hassler, "Fast Turnaround Multilayer Co–fired Ceramic Mother–board Fabrication", Proceedings of ASM's 2nd Electronic Packaging: Materials and Processes Conference, Oct. 1985, pp. 117–121.

* cited by examiner

*Primary Examiner*—Max F. Hindenburg
*Assistant Examiner*—Navin Natnithithadha
(74) *Attorney, Agent, or Firm*—Girma Wolde-Michael; Daniel C. Chapik; Michael C. Soldner

(57) ABSTRACT

An improved implantable sensor system is disclosed that includes an array of sensors. Each of the sensors is associated with a protective member that prevents the sensor from interacting with the surrounding environment. At a selected time, the protective member may be disabled, thereby allowing the sensor to begin sensing signals within a living body. In one embodiment, the protective member is formed of a conductive material that can oxidize, is biocompatible, bioabsorbable, and that may be dissolved in solution such as blood upon application of an electric potential. In another embodiment, the protective member is formed of a dissolvable member that dissolves within the body over a predetermined time period.

30 Claims, 7 Drawing Sheets

SENSOR SYSTEM

RELATED APPLICATIONS

The current invention is relative to provisionally-filed application Ser. No. 60/260,237 filed Jan. 8, 2001, which is incorporated herein by reference in its entirety.

BACKGROUND OF THE INVENTION

Implantable electrochemical sensors have become an important tool for analyzing and quantifying the chemical composition of a patient's blood. For example, glucose sensors are generally employed to measure blood glucose levels in patients having diabetes. Such measurements may be used to monitor patient condition, as well as to modify a treatment regimen which typically includes the regular administration of insulin. Thus, blood glucose readings are particularly useful in optimizing therapy.

Electrochemical sensors may be used to obtain periodic readings over an extended period of time. For example, small, flexible subcutaneous sensors are available for chronic implant to perform measurements over time. Such subcutaneous sensors are manufactured using thin film mask techniques. Sensors manufactured according to this process include thin film conductive elements encased between flexible insulative layers of polyimide sheets or similar material. These sensors typically include a plurality of exposed electrodes at one end for subcutaneous placement within a user's blood. The other end of the sensor generally includes a corresponding exposed plurality of conductive contacts that are adapted to be coupled to a monitoring device. Typical thin film sensors are described in U.S. Pat. Nos. 5,390,671, 5,391,250, 5,482,473, and 5,586,553.

Conventional implantable sensors of the type described above have several disadvantages. Such sensors are generally adapted to be located in contact with subcutaneous tissue for an extended length of time. Extended contact with bodily fluids may cause electrodes provided by the sensors to degrade, resulting in inaccurate sensor readings. Additionally, conventional implantable sensors are generally susceptible to electromagnetic interference, degrading sensor performance. Finally, because of the limited communication capabilities associated with most sensors, direct remote monitoring of sensor signals is not possible, and some intermediate device is necessary to provide the long-range communication capability.

What is needed, therefore, is an improved subcutaneous sensor that addresses the foregoing disadvantages.

SUMMARY OF THE INVENTION

The present invention provides an improved implantable sensor system for sensing signals within a living body. The system includes an array of sensors. One or more of the sensors in the array is associated with a protective member that prevents the associated sensor from interacting with the surrounding environment. At a selected time, the protective member may be disabled, thereby allowing the sensor to begin operating to provide sensed signals. In one embodiment, the protective member is formed of a conductive material that can oxidize, is biocompatible, bioabsorbable, and that may be dissolved in solution such as blood upon application of an electric potential. For example, a sensor may be formed within a well of a substrate that is capped by a conductive material such as a biocompatible metal or an electrically-erodible polymer. In another embodiment, the protective member is formed using a material that dissolves over a predetermined period of time. By selecting a variety of materials to form the protective members, various sensors are activated over time to extend the life of the sensor system.

At a given time, one or more activated sensors from the sensor array may be utilized to sense signals that are then processed to provide a more accurate indication of a biological or other condition. For example, signals from multiple activated sensors may be averaged. Alternatively, a voting scheme may be utilized such that one or more signals are discarded prior to obtaining an average signal value. Any other processing scheme may be utilized to obtain a measurement that may then be used to monitor a patient's condition, or modify therapy delivery.

In one embodiment, the sensor system includes a therapy delivery system for providing therapy based on one or more of the sensed signals. The therapy delivery system may include a drug pump, a circuit to provide electrical stimulation to tissue, or any other type of therapy delivery means known in the art.

According to one aspect of the invention, the disclosed sensor system includes a sensor to sense a biological indicator, and a protective member located adjacent the sensor to shield the sensor from a surrounding environment for a selectable time period. According to another aspect of the invention, a method of sensing signals within a living body is disclosed. The method includes providing a sensor, providing a protective member to prevent the sensor from interacting with the living body, selectively disabling the protective member, and obtaining at least one signal from the sensor. Other aspects of the invention will become apparent from the following description and the attached drawings.

DETAILED DESCRIPTION OF THE DRAWINGS

Figure 1:
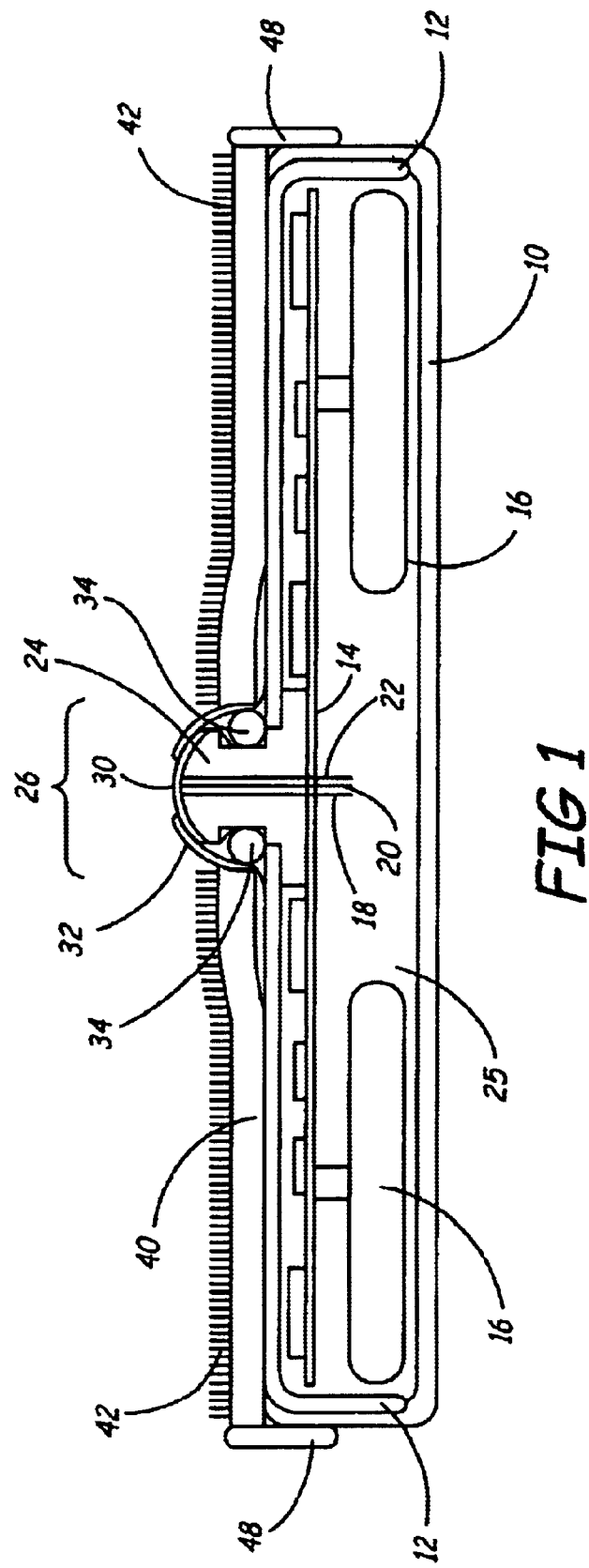
FIG. 1 is cross-sectional view of an exemplary glucose sensor as may be adapted for use with the current invention.

FIG. 1 is cross-sectional view of an exemplary glucose sensor as may be adapted for use with the current invention. This type of glucose sensor, which is described in U.S. Pat. No. 6,001,067, may be placed subcutaneously to perform long-term monitoring of glucose levels in the blood. The sensor includes a housing that defines a cavity. The housing includes a bottom portion 10 and a top portion 12 that engages the bottom portion. The housing may enclose electronic circuitry as is shown provided on a circuit board 14. This circuitry may be powered by one or more batteries 16, or alternatively, may receive power via implanted medical electrical leads coupled to another implantable medical device (IMD) as will be described below. Any electronic circuitry adapted to provide long-term continuous monitoring may be used in conjunction with the device of the present invention.

Circuit board 14 is shown coupled to three electrodes, including a silver reference electrode 18, a platinum working electrode 20, and a platinum counter electrode 22. The use of such electrodes in glucose monitoring systems is known in the art, however, the present invention is neither limited by the composition of the electrodes nor their position within the sensor system. The electrodes are surrounded by an electrically-insulative material 24 such as a structure formed of an epoxy insulation.

The housing of the devices of the present invention may use a packaging technique that protects the components of the device in aqueous media. For example, the top and bottom portions of the housing may be manufactured from a thermoformed high-density polyethylene. The area inside the housing surrounding the electronic circuit board 14 and other components may be filled with a material 25 that cushions the system while not interfering with circuit operation. Material 25 may be a mixture of petroleum wax and low melting temperature resins, for instance.

The electrodes may extend through an opening in top portion 12 into a dome structure 26. While this dome structure is not required, it is believed to enhance interaction of the sensor with surrounding fluid and tissue, thereby increasing accuracy of the sensor readings.

Electrodes extend to a membrane structure 30 which may include multiple membranes as is known in the art. For example, membrane structure may include an inner membrane that contains an enzyme, such as glucose oxidase. One or more polymer layers, and/or an additional bioprotective layer may be added to protect the sensor from external forces that may result in environmental stress cracking of the enzyme membrane Finally, an angiogenic layer may be included to promote vascularization in the sensor interface region.

Membrane structure 30 is maintained in position via a sheath 32, which may extend over a portion of the membrane structure as shown. Attachment of membrane structure may be further accomplished using a gasket 34 formed of silicon rubber or another similar material. Gasket 34 also aids in forming a seal around the membrane.

In one embodiment of the invention, the sensor may further include a top sheath 40 that covers the top portion 12. For a subcutaneous sensor, top sheath may be coated with a layer 42 of material that promotes tissue in-growth to stabilize the sensor position and to ensure an adequate blood supply near the sensor. Layer 42 may be formed of materials including, but not limited to, polyester, poly(ethylene terephthalate)) velour, expanded polytetrafluoroethylene, polytetrafluoroethylene felts, polypropylene cloth, and related porous implant materials.

The sensor of FIG. 1 is further shown to include side braces 48 to secure top sheath 40 to bottom portion 10. Additional aspects of the exemplary sensor system are described in U.S. Pat. No. 6,001,067.

Figure 2:
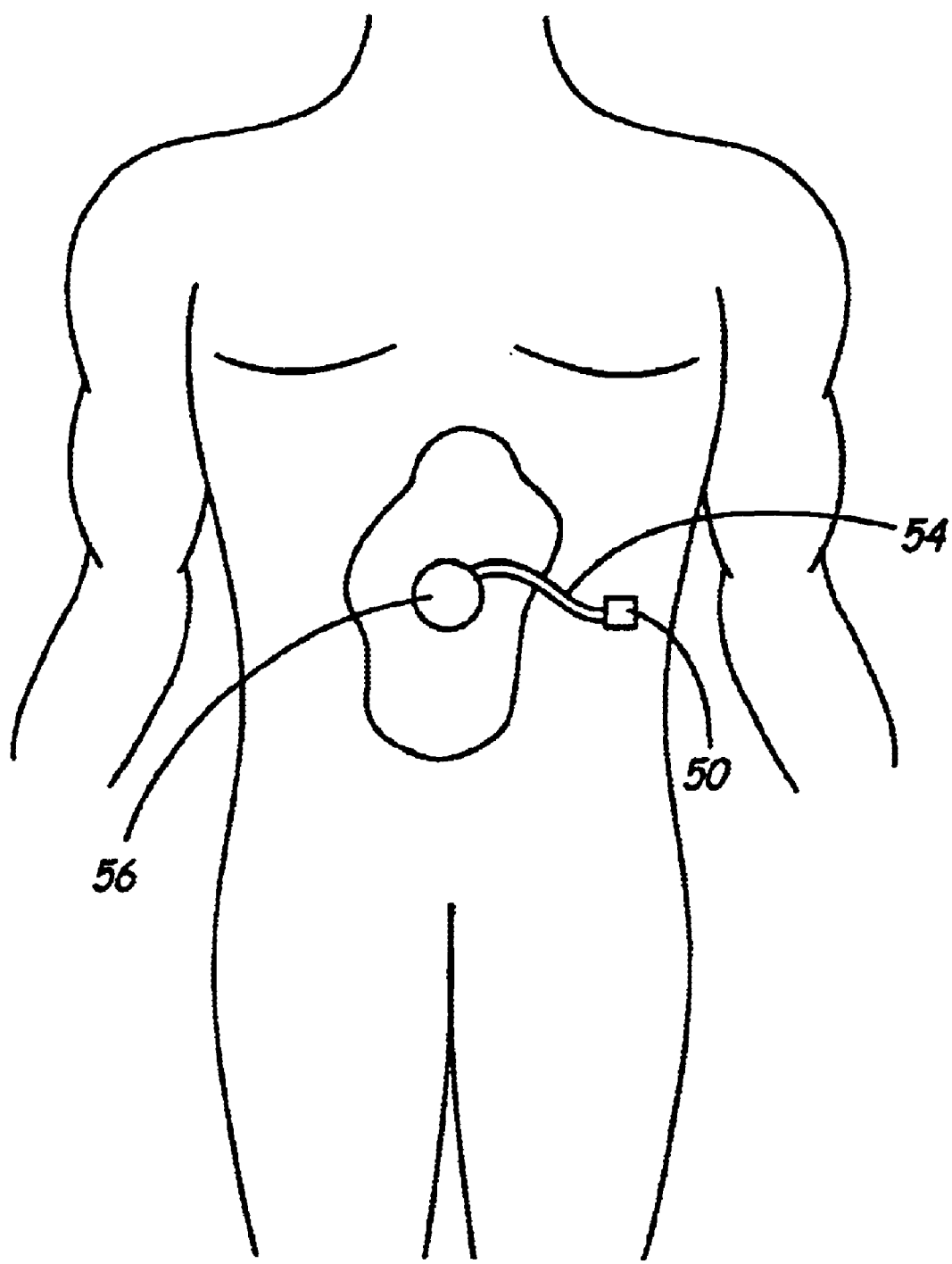
FIG. 2 is a diagram illustrating a sensor such as that shown in FIG. 1 carried on a medical electrical lead and coupled to an implantable medical device.

FIG. 2 is a diagram illustrating a sensor 50 such as that shown in FIG. 1 carried on a medical electrical lead 54 and coupled to an implantable medical device (IMD) 56. In this embodiment, the circuitry of the sensor system such as that associated with circuit board 14 (FIG. 1) may receive some or all of its power from IMD 52, and batteries 16 may not be needed. Additionally, some of the circuitry associated with the sensor system may be incorporated into circuitry housed within IMD 52. Sensor 50 may be located subcutaneously as discussed above, or may be positioned in another location within the body as required such as within a vein like the superior vena cava.

As discussed above in reference to FIG. 1, membrane structure 30 may include several different layers and membranes that cover the electrodes of the sensing device. These layers and membranes are semi-permeable, preventing direct contact of the biological fluid sample with the electrodes, while permitting substances such as glucose to diffuse through the membrane structure so that an electrochemical reaction may occur when a DC bias voltage is placed across the electrodes. Examples of materials that may be used to form semi-permeable membranes include, but are not limited to, polyethylene, polyvinylchloride, polytetrafluoroethylene, polypropylene, polyacrylamide, cellulose acetate, polymethyl methacrylate, silicone polymers, polycarbonate, and cellulosic polymers. The present invention is not limited by the nature or type of the semi-permeable membranes used in the sensor interface region.

The semi-permeable membranes selected for membrane structure 30 have pores sized to allow glucose molecules to diffuse into the cavity of the sensor. These glucose molecules may be catalytically converted in the presence of oxygen and water to gluconic acid and hydrogen peroxide. This electrochemical reaction is facilitated by the enzyme glucose oxidase provided on the inner membrane of membrane structure 30. During this reaction, oxygen is depleted while hydrogen peroxide is created in proportion to the amount of glucose in the blood. Thus, the glucose level in the blood may be monitored by sensing oxygen depletion, or alternatively, by sensing the increased levels of the hydrogen peroxide. In one embodiment, each of the sensors 102 includes an oxygen sensor that monitors the depletion of oxygen in the blood as an electrochemical reaction takes place with glucose, water, and oxygen molecules when a DC bias voltage is placed across the electrodes. The oxygen levels so measured are compared to a control oxygen level measured by oxygen sensor 149 to determine glucose levels within the blood. In another embodiment, a DC bias voltage is placed across the electrodes and a current is read. This current is the result of production of hydrogen peroxide, which is anodically active. Because the induced current is directly proportional to the concentration of hydrogen peroxide, which, in turn, is proportional to the concentration of glucose in the sample, glucose levels may be determined. This is discussed in U.S. Pat. Nos. 4,757,022 and 4,994,167 to Shults et al.

One problem associated with glucose sensors involves the deterioration of the glucose oxidase that is used as the catalyst in the electrochemical reaction. Exposure of the sensor to high levels of hydrogen peroxide degrades the glucose oxidase. Moreover, glucose oxidase is subject to deactivation as a function of ambient conditions. Because of this effect, some studies have shown that when placed in a saline solution at 37° C., glucose electrodes may lose half of their electrode enzyme activity in 85 to 105 days. Under reasonable diabetic conditions and normal enzyme loading, useful sensor lifetimes may be limited to approximately one year. However, replacing an implanted sensor after only a year of use is highly undesirable. The current invention addresses this problem by providing a sensor array that allows for the selective activation of individual sensors over time.

Figure 3:
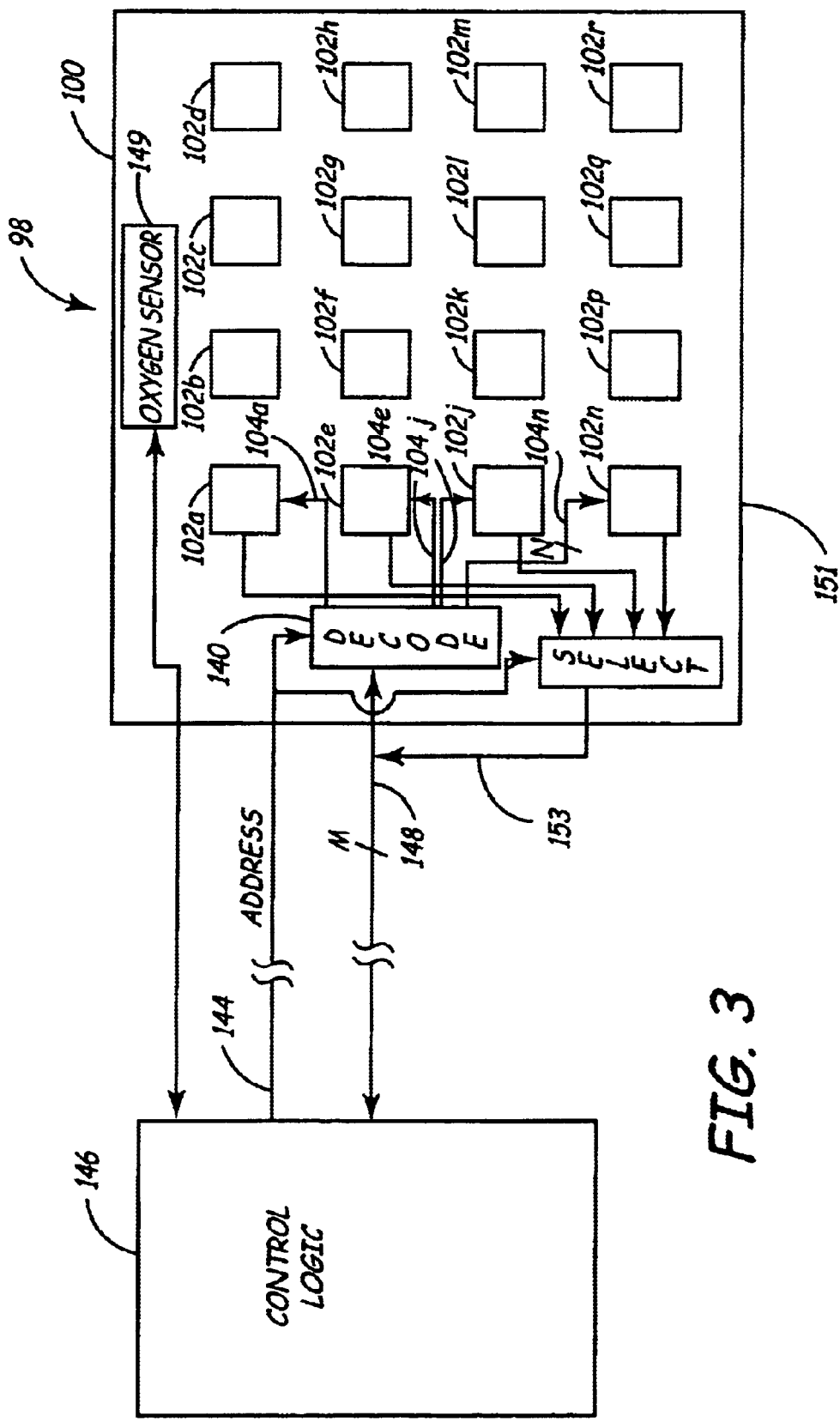
FIG. 3 is a block diagram of the sensor array.

FIG. 3 is a block diagram of the sensor array 98 according to the current invention. The system includes a substrate 100 that supports an X×Y array of sensors shown as sensors 102a–102r. Although sixteen such sensors are shown, any other number of sensors as may be supported by substrate 100 is possible. Each of the sensors may be a glucose sensor of the type discussed above in reference to FIG. 1, or another type of sensor. Each sensor is coupled to a set of N control lines 104. (For simplicity sake only several such sets of control lines 104a, 104e, 104j, and 104n are shown.) Each set of control lines 104 is driven by a decode circuit 142. The decode circuit activates one or more sets of the control lines 104 based on one or more addresses placed on address lines 144 by control logic 146. In one embodiment, only a single set of control lines 140 is activated at one time. In another embodiment, multiple sets of the control lines may be activated at once. These control lines allow the selected sensors to become operational in a manner to be discussed further below.

To read signals from one or more activated sensors, a select circuit 151, which may be a multiplexer, may be enabled to select sensor signals driven by the sensor(s). The selected sensor signals are then provided on lines 153 and 148 may then be provided to control logic 146 for processing. If desired, select circuit 151 and control lines 153 and 148 may be adapted so that signals from multiple sensors may be obtained simultaneously. Alternatively, addresses may be provided in a sequential manner so that sensor signals are obtained in a time-multiplexed manner. In the latter case, the time multiplexing minimizes interference from adjacent sensor signals, and thereby may provide more accurate measurements.

It may be noted that control logic, decode circuit 140, and/or select circuit 151 may be located within the sensor 50, or in IMD 56 which is coupled to the sensor via a lead such as lead 54. In the latter case, the signals coupling control logic 146 to the sensor are carried by lead 54.

In one embodiment, each sensor must be activated prior to use by applying appropriate signals on associated control and address lines to remove a protective member adjacent to the sensor in a manner to be discussed below. Prior to activation, a sensor is not exposed to the surrounding environment, so degradation does not occur. After the protective member is removed, sensing may be performed with the sensor until such a time as the sensor performance is determined to be degrading and outside a pre-defined range of accuracy. Thereafter, the sensor may be left unused and a different sensor activated in its place. In this manner, the inventive implantable sensor system may be utilized for years without requiring replacement.

Figure 4A:
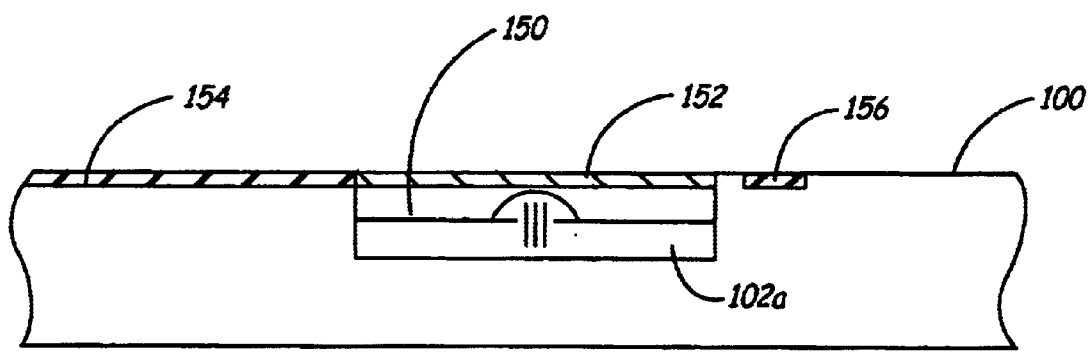
FIG. 4A is a cross-sectional view of one embodiment of a sensor according to the current invention.

FIG. 4A is a cross-sectional view of one embodiment of a sensor for use within the current invention. In this embodiment, sensor 102a is shown formed within a well 150 formed in substrate 100. Protective member 152 is formed over the well to prevent the sensor from being exposed to bodily fluids prior to a predetermined time. In one embodiment, the protective member consists of a thin film of conductive material sized to cover well 150. In another embodiment, the thin film may extend beyond the edge of well to partially cover substrate 100. Any conductive material that can oxidize, is biocompatible, bio-absorbable, and that may be dissolved in solution such as blood upon application of an electric potential can be used for the fabrication of protective member 152. Examples of such materials include copper, gold, silver, and zinc, and some polymers, as described, for example, by I. C. Kwon et al., "Electrically Erodible Polymer Gel for Controlled Release of Drugs", Nature, 1991, 354, 291–93; and Y. H. Bae et al., "Pulsatile Drug Release by Electric Stimulus", ACS Symposium Series, 1994, 545, 98–110 incorporated herein by reference.

Protective member 152 may be formed by injection or spin coating. Alternatively, well 150 can be capped by capillary action, by drawing the material partially into the well with a vacuum or other pressure gradient, by melting the material into the well, by centrifugation and related processes, by inserting solids into the well, or by any combination of these or similar methods.

Protective member 152 is electrically and mechanically coupled to a respective conductor such as conductor 154 referred to as the anode. An additional "cathode" conductor 156 is located adjacent to, but electrically and mechanically isolated from, a respective reservoir. Both the cathode and anode are included within those signals shown collectively as control lines 148 and 104a of FIG. 3. A voltage difference applied across anode 154 and cathode 156 when the protective member is placed in a conductive solution causes electrons to pass from the anode conductor to the cathode conductor through the conductive solution. This, in turn, causes the protective member, which may be considered the anode of the circuit, to oxidize and dissolve into the surrounding fluids, exposing the sensor to surrounding body fluids so that the sensor becomes operational.

Figure 4B:
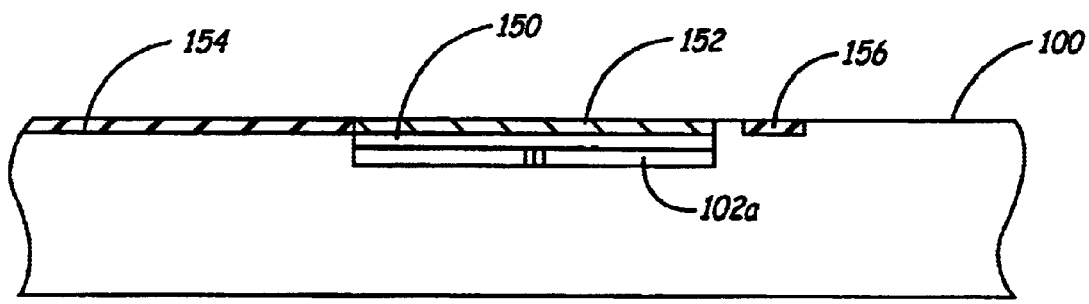
FIG. 4B is a side view of another embodiment of sensor including a protective member according to the current invention.

FIG. 4B is a side view of another embodiment of sensor 102a including protective member 152. In this embodiment, sensor 102a does not include optional dome structure 26, and well 150 may therefore be formed in a more shallow manner. This allows sensor dimensions to be minimized. In yet another embodiment, protective member 200 may be deposited directly on sensor 102a. In this embodiment, membrane materials must be selected that are not affected by the deposition and subsequent removal of the protective member 152.

Figure 5:
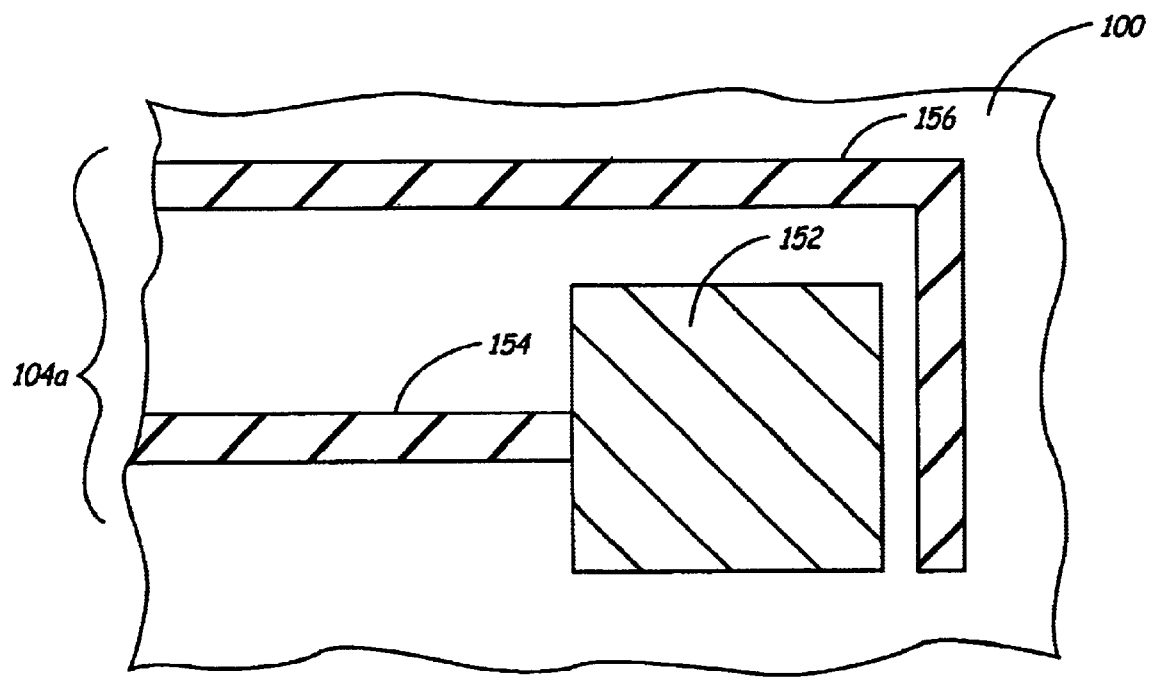
FIG. 5 is a top view of one embodiment of a sensor having a protective member and showing the routing of an anode and a cathode.

FIG. 5 is a top view of one embodiment of substrate 100 including protective member 152 of sensor 102a, and illustrating the routing of anode 104 and cathode 106. In this view, sensor 102a is not visible. Each of the sensors 102a–102r of FIG. 3 are associated with similar routed nets, although this routing is not shown in FIG. 3 for simplicity. Each sensor may be individually addressable so that a single sensor may be activated at a given time. Since the protective member may require some time to dissolve after a potential difference is applied across the respective anode and cathode, a preferred embodiment activates a second sensor during a time period when a first sensor is activated and still usable. In another embodiment, a single anode/cathode pair is used to activate multiple sensors by removing or disabling each of the respective protective members. This allows an entire sensor bank to be activated at once. In yet another embodiment, multiple sensors may be associated with a single protective member. For example, multiple sensors may be included within a single well such as well 150 so that disabling or dissolving one protective member will enable each of the multiple sensors.

Although the foregoing examples described protective member that dissolve or erode through the use of a current, any bio-absorbable material that it dissolves within a body in a predictable time period may be utilized. For example, one or more first sensors may be left uncoated, while one or more additional sensors may be associated with a respective protective member that substantially absorbs over a first time period. Yet another set of sensors may each be associated with protective members formed of another material known to substantially dissolve over a second time period which is longer than the first time period, and so on.

Regardless of the type of protective member utilized, sensor measurements may be obtained after the protective member is dissolved or otherwise eroded. In one embodiment, time multiplexing may be used to obtain multiple sensor readings. As discussed above, control circuit 146 can sequentially enable predetermined activated ones of the sensors 102 by applying various addresses on address line 144 in a time multiplexed manner. Multiple measurements are thus obtained that may thereafter be processed in any desired manner. For example, multiple sensor readings may be used to obtain an average. Alternatively, a voting scheme may be used to discard a measurement that is determined to be out-of-range as compared to the other measurements. If desired, a first predetermined number of sensor readings that are farthest away from the overall average may be discarded with the remaining readings being averaged.

According to another aspect of the invention, processing may be performed to determine when a given sensor is deteriorating. For example, if one or more measurements from a given sensor are outside of a range established by other sensor measurements, the out-of-range sensor may be thereafter unused and another sensor activated. Alternatively, a sensor may be enabled for a predetermined period of time, then automatically disabled.

Figure 6:
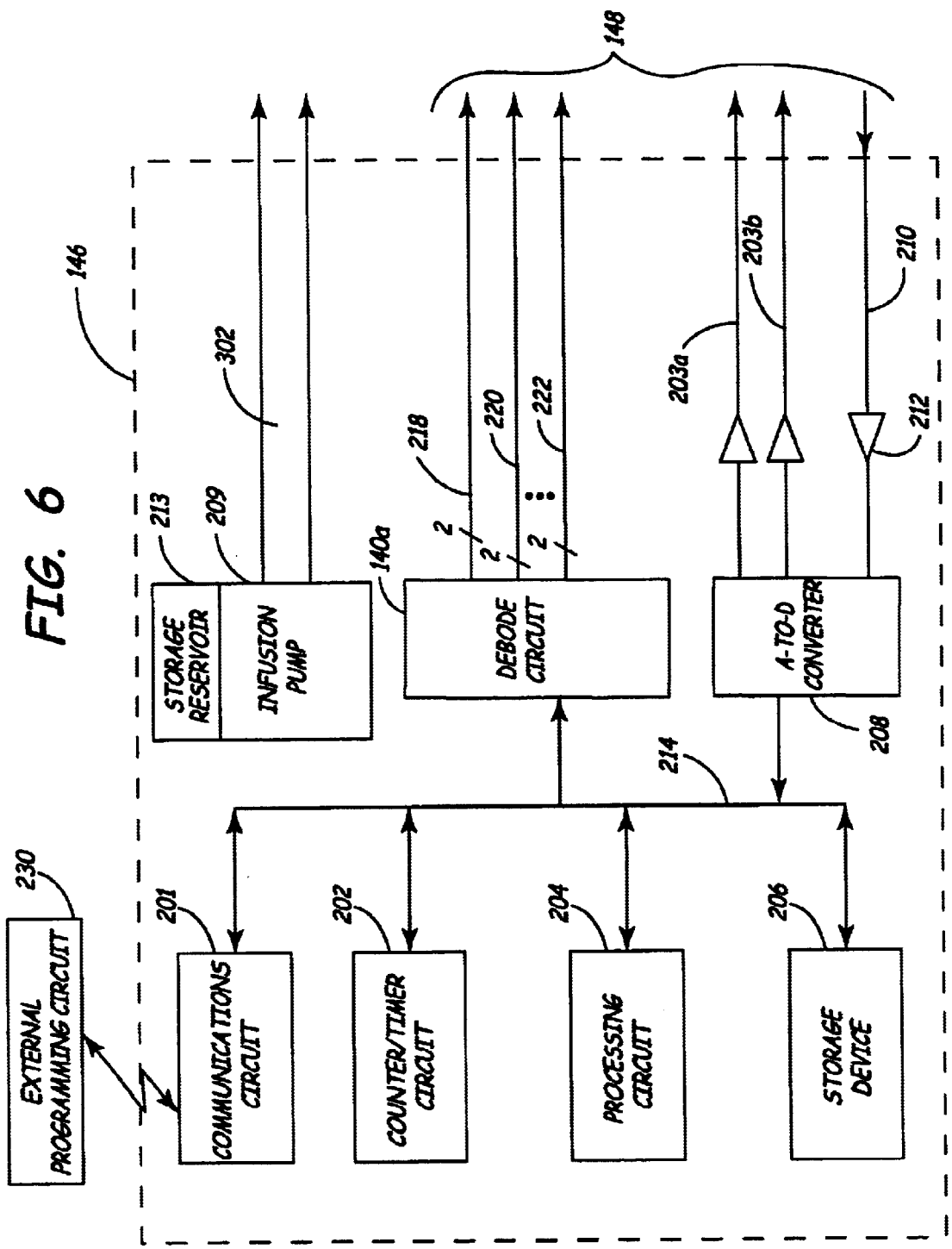
FIG. 6 is system block diagram of one embodiment of control circuit as may be used with the current invention.

FIG. 6 is system block diagram of one embodiment of control circuit 146 as may be used with the current invention. Control circuit 146 may be provided within any implantable medical device (IMD) known in the art, such as IMD 56 of FIG. 2. For example, control circuit 146 may include circuitry for delivering electrical stimulation for pacing, cardioversion, and/or defibrillation purposes on electrical stimulation outputs 203a and 203b.

Control circuit may include a communications circuit 201 such as a telemetry system such as described in commonly-assigned U.S. Pat. No. 6,169,925 entitled "Telemetry System for Implantable Medical Devices", incorporated herein by reference in its entirety. The use of this telemetry system within the sensor array would provide a system capable of long-range communication with personal patient communication devices. Such patient communication devices may have an audible alarm function to alert the patient of sensor readings outside a range considered acceptable. The audible alarm may also include tones to inform the user of actions that should be taken by the user in response to an original alert. The level of urgency of the alarm could also be encoded into the tonal signal changes. Additionally, the patient could be informed of information through muscle or nerve stimulation from additional electrodes on the device. In another embodiment, a telemetry signal may be provided to an external device to deliver an automatic alert in the event an emergency situation is detected. For example, if conditions indicate a patient is entering a diabetic shock condition, emergency workers may be automatically contacted via an uplink to a communications system. Patient data may automatically be provided to emergency healthcare workers using information stored within storage device 206. If desired, an associated Global Positioning System (GPS) may provide patient location data.

Control circuit may further include a counter/timer circuit 202, a processing circuit 204, and a storage device 206. Counter/timer circuit 202 may be utilized to generate the pacing and/or cardioversion/defibrillation pulses that may be provided via optional electrical stimulation outputs 203.

Processing circuit 204 may be a microprocessor or other processing circuit as is known in the art. Storage device may comprise Random Access Memory (RAM), Read-Only Memory, registers, a combination thereof, or any other type of memory storage device suitable for use in implantable medical devices. Control circuit 146 may further include an Analog-to-Digital (A-to-D) converter 208, which receives input signals from one or more of the implantable sensors 102 according to the current invention.

An IMD used in accordance with the current invention may also include a drug infusion pump such as pump 209 coupled to one or more drug delivery catheters such as catheter assembly 302. Pump 209 pumps a biologically-active agent stored within remote storage reservoir 213 through an inner lumen of catheter 102 in a manner prescribed by a predetermined drug therapy regimen. Such a pump may be an implantable drug infusion pump with a programmable flow rate such as the SynchroMed pump commercially available from Medtronic Corporation. The SynchroMed is an internally-powered programmable pump having features which allow physicians to change fluid delivery parameters, such as flow rate, infusion period, ramp time, and bolus volume. As an alternative, an implantable pump such as that described in commonly assigned U.S. Pat. No. 5,820,589, incorporated herein by reference, may be utilized. This alternative design provides a pump that is programmed non-invasively by means of a programmer that communicates flow rate information by means of radio frequency telemetry or other methods of non-invasive telemetry. The programmer also supplies power to the implantable pump during programming so that battery power is not required.

In one embodiment of the invention, the drug delivery system operates in a closed-loop mode wherein one or more sensor signals received from one or more of the sensor inputs 210 as received from sensor array 98 (FIG. 3) may trigger the delivery of biologically-active agent such as insulin to a patient. These sensor inputs 210 are included within those signals shown collectively as control line 148 of FIG. 3. In this mode, one or more sensor signals may be amplified by amplifier circuit 212, converted to digital format by A-to-D converter 208, and provided to processing circuit 204. Operating under software and/or hardware control, processing circuit processes the received signal(s) to determine a course of action. As discussed above, processing circuit may average one or more sensor readings, or may use a voting scheme to discard out-of-range signals prior to determining the course of action.

In one embodiment, storage reservoir 213 coupled to the infusion pump may be refillable via a port for receiving a syringe. If control circuit 146 is included within an IMD that is subcutaneously located, the syringe may be inserted through subcutaneous tissue into the port to refill reservoir when the reservoir become partially or completely empty. An audible or other type of alarm may be provided to notify a patient when the reservoir has reached a predetermined fill level.

In this embodiment, decode circuit 140 of FIG. 3 is included within the IMD, and is shown as decode circuit 140a. This circuit is provided to selectively activate one or more anode/cathode pair such as anode 254 and cathode 256 of FIGS. 4A and 4B. These anode/cathode pairs are shown as pairs 218 through 222, although additional pairs may be provided for each sensor 102, or for groups of sensors. These anode/cathode pairs are included within signal lines 148 and 104 of FIG. 3.

Figure 7:
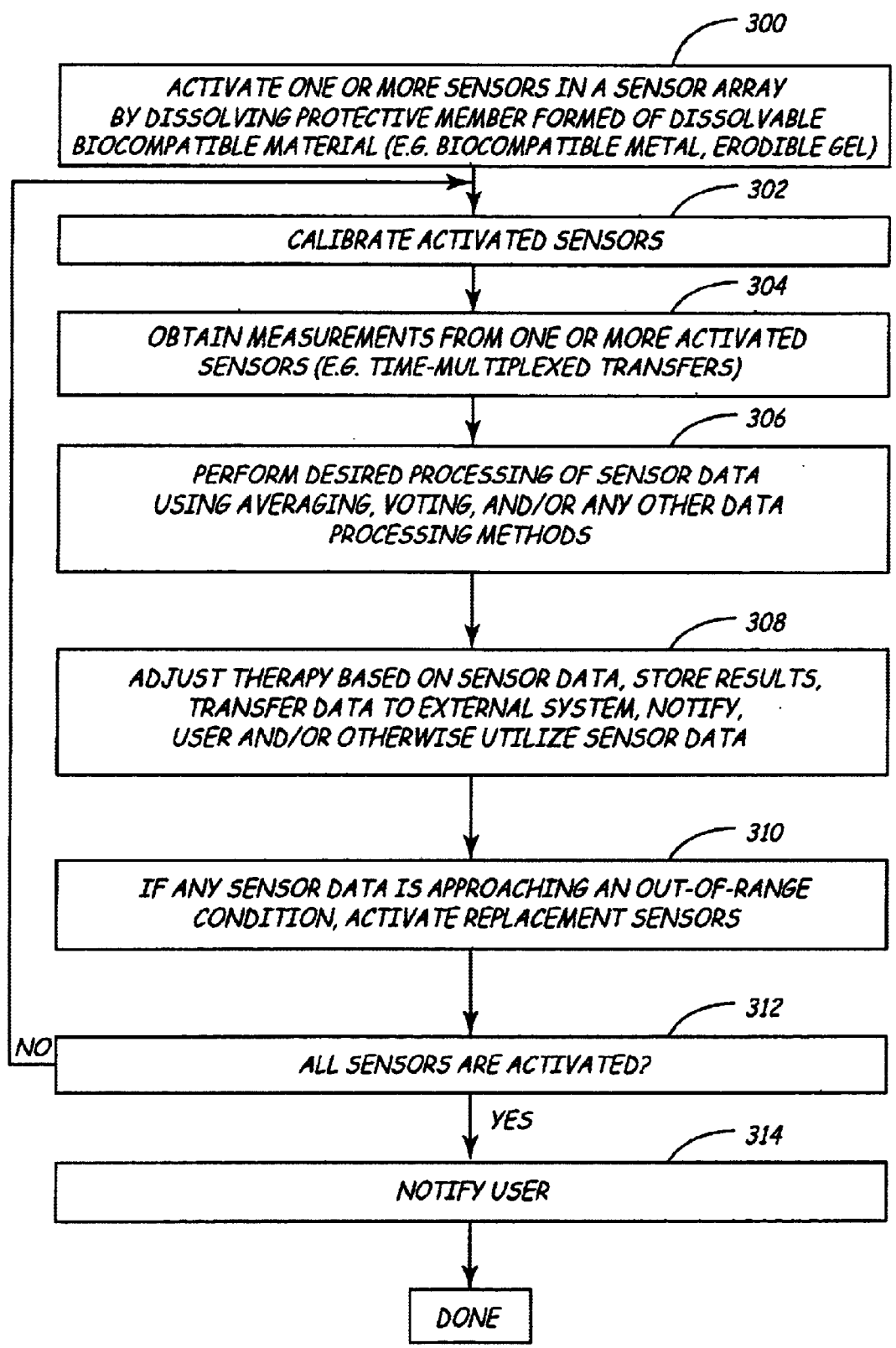
FIG. 7 is a flow diagram illustrating one embodiment of a method as may be practiced with the current invention.

FIG. 7 is a flow diagram illustrating one embodiment of a method as may be practiced with the current invention.

After the sensor array is positioned either subcutaneously or within another location within a patient, one or more sensors may be selected for activation (300). As discussed above, activation of a sensor is accomplished by utilizing an associated anode/cathode pair to dissolve or otherwise remove an associated protective member 152, exposing the sensor to the environment. The protective member 152 may be formed of any bio-compatible, dissolvable material such as biocompatible metal or erodible polymer gel. Alternatively, a material that dissolves over time may be utilized to selectively expose one or more electrodes over a given time period. Since the activation process may require a certain amount of time to complete, this process is preferably initiated prior to the time sensor use is required. Thereafter, the sensor may be calibrated by control circuit 146. This could be accomplished by adjusting operational amplifiers, or adjusting control signals associated with the sensor, as is known in the art (302).

Once a sensor is activated, it may be used to obtain measurements (304). Multiple sensors may be utilized to obtain multiple measurements, with the measurements being processing, if desired, to derive a single representative measurement (306). This processing may involve an averaging scheme, a voting mechanism wherein one or more measurements are discarded, a combination thereof, or any other processing mechanism for obtaining a representative measurement utilizing the obtained sensor data.

Data obtained in the foregoing manners may be utilized as desired to modify therapy, or to notify the user of a sensed condition (308). These signals may be stored either within the IMD or an external system to develop trend data. As discussed above, the data may be used within a closed-loop system to adjust drug delivery, to adjust electrical stimulation provided to a patient, or to alter therapy in any other required manner.

Data obtained using the sensor measurement may also be utilized to monitor sensor performance (310). For example, predetermined sensor measurement ranges may be defined to determine when a sensor is approaching an out-of-range condition. This out-of-range situation can also be detected by comparing a sensor measurement to measurements obtained from other ones of the sensors. Regardless of the mechanism used, an approaching out-of-range condition may trigger the activation of one or more additional sensors as replacements. When all sensors are activated, a notification may be provided indicating an elective replacement procedure may be required (312, 314). Otherwise, processing continues with the calibration of the newly-activated sensors (302).

According to another aspect of the invention, interference associated signals obtained from sensor array 98 may be minimized. As noted above, this may be accomplished, in part, by time-multiplexing signals from various sensors so that interference between signals during simultaneous signal transmission does not occur. Another method for minimizing electromagnetic interference involves using sensor electrodes that are optimized by shape and orientation with respect to one another. For example, the sensor of FIG. 1 includes three electrodes 18, 20 and 22. These electrodes could be oriented as concentric rings or in another symmetrical pattern. By utilizing symmetry in this manner, all electrodes are affected in a substantially similar manner by electromagnetic disturbances. This minimizes the possibility that a local disturbance will affect one electrode reading more than another, providing skewed results. Additionally, the surface area of the electrodes may be increased to decrease the source impedance of the measurements.

As will be appreciated, sensor array 98 includes more conductive traces than are included in conventional sensor systems that contain only a single sensor. To accommodate the higher trace density, a multi-layer substrate and feedthrough system having aspects similar to those discussed in U.S. Pat. Nos. 5,782,891 and 4,991,582, both incorporated herein by reference in their entirety, may be utilized. According to one embodiment of this arrangement, a ceramic enclosure may be provided which is composed of biocompatible 99.5 percent aluminum oxide. A thin film of niobium may be provided on the ceramic surface, which may be deposited using a sputtering process, for example. Also provided is a multi-layered feedthrough substrate having several layers of ceramic material with metal-plated input/output vias used to electrically connect the various layers. The plating metals may be gold and nickel, for example. As a result of the multi-layer and via configuration, a higher density of feedthroughs is possible as compared to a conventional glass-to-metal feedthrough substrate approach. The substrate can be constructed using techniques known in the art, such as is disclosed by Beth A. Hassler in "Fast Turnaround Multilayer Co-fired Ceramic Mother-Board Fabrication," Proceedings of ASM's 2nd Electronic Packaging: Materials and Processes Conference (October 1985): 117–121 which is incorporated herein by reference.

Weld rings having thermal expansion characteristics sufficiently similar to the ceramic material are used to maintain superior bonding over a broad temperature range. One weld ring is brazed to the multi-layered feedthrough. The welded and brazed surfaces complete a hermetic seal of the sensor. Using a feedthrough mechanism similar to that shown in the '891 patent, the O-rings and epoxy insulation utilized by previous sensor designs may be eliminated, and the sensor size may be reduced. Additionally, the hermaticity of the sensor is improved.

When using a ceramic structure such as that shown in the '891 patent referenced above, the electrodes may be shaped to be flat with respect to the ceramic surface. This allows one or more of the various layers included in the membrane structure 30, including the electrolyte, the enzyme, bioprotective, and/or angiogenic layer, to be applied using spin coating or other standard methods.

Although the above description discusses the use of glucose sensor with the current invention, any sensor that degrades over time when in contact with a living body or when activated in general may usefully be employed within the inventive sensor array system, and may further incorporate one or more of the inventive aspects of the system as discussed above. Additionally, multiple different types of sensors for sensing different biological indicators, signals, and/or agents may be incorporated into a sensor array. Therefore, the above description should be considered exemplary in nature.

What is claimed is:

1. A sensor system, comprising:
    a sensor to sense a biological indicator;
    a protective member located adjacent the sensor to shield the sensor from a surrounding environment for a selectable time period; and
    a processing circuit in communication with the sensor to receive a signal of the biological indicator and to indicate a therapy to be delivered.

2. The sensor system of claim 1, and further including a control circuit coupled to the protective member to disable the protective member after the selectable time period.

3. The sensor system of claim 2, wherein the protective member is formed of biocompatible metal.

4. The sensor system of claim 2, wherein the protective member is formed of erodible polymer gel.

5. The sensor system of claim 1, wherein the protective member is formed of a material that substantially dissolves within a living body over the selectable time period.

6. The sensor system of claim 2, wherein the control circuit includes a cathode and an anode to cause a current to flow through the protective member.

7. The sensor system of claim 2, and further including multiple sensors, each associated with a protective member, and wherein the control circuit includes a circuit capable of selectively disabling one or more of the protective members.

8. The sensor system of claim 7, wherein the control circuit includes a processing circuit to determine when operation of any of the multiple sensors is degrading.

9. The sensor system of claim 8, wherein the control circuit includes an alarm to provide an indication to a user based on signals provided by one or more of the multiple sensors.

10. The sensor system of claim 7, wherein the multiple sensors are each glucose sensors.

11. A system for sensing a biological agent, comprising:
at least two sensors; and
at least two protective members, each being associated with a respective one of the sensors to prevent the respective sensor from interacting with a surrounding environment.

12. The system of claim 11, and further including a control circuit to disable one or more selected ones of the at least two protective members, whereby one or more respective sensors are activated to interact with the surrounding environment.

13. The system of claim 10, wherein the control circuit includes a processing circuit to process sensor signals provided by the one or more activated sensors.

14. The system of claim 13, wherein the processing circuit includes means to discard one or more of the sensor signals prior to processing remaining sensor signals.

15. The system of claim 13, and further including a therapy delivery system coupled to the control circuit to provide therapy to a patient based on the sensor signals.

16. The system of claim 15, wherein the therapy delivery system includes a drug pump.

17. The system of claim 15, wherein the therapy delivery system includes a circuit to deliver electrical stimulation to a patient.

18. The system of claim 13, wherein the control circuit includes a circuit to obtained the sensor signals in a time-multiplexed manner.

19. A method of sensing signals in a living body, comprising:

a.) providing a sensor;

b.) providing a protective member to prevent the sensor from interacting with the living body;

c.) selectively disabling the protective member;

d.) obtaining at least one signal from the sensor; and e.) determining a therapy to be delivered to the living body based on the obtained signal from the sensor.

20. The method of claim 19, wherein step c.) includes using an electrical current to cause the protective member to dissipate.

21. The method of claim 19, wherein step b.) includes providing a protective member that is dissolvable within the living body within a predetermined period of time, and step c.) includes exposing the protective member to the living body.

22. The method of claim 19, and further comprising:

providing multiple sensors;

providing multiple protective members; and disabling at least one of the multiple protective members to activate a selected one or more of the multiple sensors.

23. The method of claim 22, wherein step d.) includes obtaining multiple signals from activated ones of the multiple sensors.

24. The method of claim 23, and further including processing the multiple signals.

25. The method of claim 24, and further including discarding selected ones of the multiple signals that are determined to be outside of a pre-defined signal range.

26. The method of claim 24, and further including determining that one or more of the multiple sensors are becoming degraded based on the multiple signals.

27. The method of claim 26, and further including disabling at least one additional one of the multiple protective members to activate a selected one or more additional ones of the multiple sensors to replace sensors becoming degraded.

28. The method of claim 23, wherein obtaining the multiple signals includes receiving signals from the activated ones of the multiple sensors in a time-multiplexed manner.

29. The method of claim 19, and further including providing therapy to the living body based on the at least one signal.

30. The method of claim 29, wherein the sensor is a glucose sensor, and providing therapy includes delivering insulin to the living body.

* * * * *

UNITED STATES PATENT AND TRADEMARK OFFICE
CERTIFICATE OF CORRECTION

PATENT NO. : 6,666,821 B2
APPLICATION NO. : 10/040827
DATED : December 23, 2003
INVENTOR(S) : Keimel It is certified that error appears in the above-identified patent and that said Letters Patent is hereby corrected as shown below:

Column, 11,
Line 27, after "environment" insert --; a processing circuit to process sensor sgnals provided by the one or more activated sensors, wherein an output of the processing circuit is used to determine a therapy to be delivered --.
Line 33, delete claim 13.

Signed and Sealed this

Eighth Day of January, 2008

JON W. DUDAS
*Director of the United States Patent and Trademark Office*

(12) EX PARTE REEXAMINATION CERTIFICATE (7334th)
United States Patent
Keimel

(10) Number: US 6,666,821 C1
(45) Certificate Issued: Jan. 26, 2010

(54) SENSOR SYSTEM

(75) Inventor: John G. Keimel, North Oaks, MN (US)

(73) Assignee: Medtronic, Inc., Minneapolis, MN (US)

Reexamination Request:
No. 90/008,413, Apr. 2, 2007

Reexamination Certificate for:
Patent No.: 6,666,821
Issued: Dec. 23, 2003
Appl. No.: 10/040,827
Filed: Jan. 8, 2002

Certificate of Correction issued Jan. 8, 2008.

Related U.S. Application Data
(60) Provisional application No. 60/260,237, filed on Jan. 8, 2001.

(51) Int. Cl.
*A61B 5/05* (2006.01)
*A61B 5/00* (2006.01)

(52) U.S. Cl. .................. 600/365; 600/345; 600/347; 600/372; 600/373; 600/377

(58) Field of Classification Search .................. None
See application file for complete search history.

(56) References Cited

U.S. PATENT DOCUMENTS

| | | | |
|---|---|---|---|
| 4,951,674 A | 8/1990 | Zanakis et al. | |
| 5,820,589 A | 10/1998 | Torgerson et al. | |
| 5,871,509 A | 2/1999 | Noren | |
| 6,058,331 A | 5/2000 | King | |
| 6,082,367 A | 7/2000 | Greeninger et al. | |
| 6,104,955 A | 8/2000 | Bourgeois | |
| 6,248,080 B1 * | 6/2001 | Miesel et al. | 600/561 |
| 6,289,328 B2 | 9/2001 | Shaffer | |
| 6,379,969 B1 | 4/2002 | Mauze et al. | |
| 6,551,838 B2 | 4/2003 | Santini, Jr. et al. | |
| 2002/0072784 A1 | 6/2002 | Sheppard, Jr. et al. | |

FOREIGN PATENT DOCUMENTS

WO 01/35928 5/2001

* cited by examiner

*Primary Examiner*—Jeanne M Clark

(57) ABSTRACT

An improved implantable sensor system is disclosed that includes an array of sensors. Each of the sensors is associated with a protective member that prevents the sensor from interacting with the surrounding environment. At a selected time, the protective member may be disabled, thereby allowing the sensor to begin sensing signals within a living body. In one embodiment, the protective member is formed of a conductive, material that can oxidize, is biocompatible, bioabsorbable, and that may be dissolved in solution such as blood upon application of an electric potential. In another embodiment, the protective member is formed of a dissolvable member that dissolves within the body over a predetermined time period.

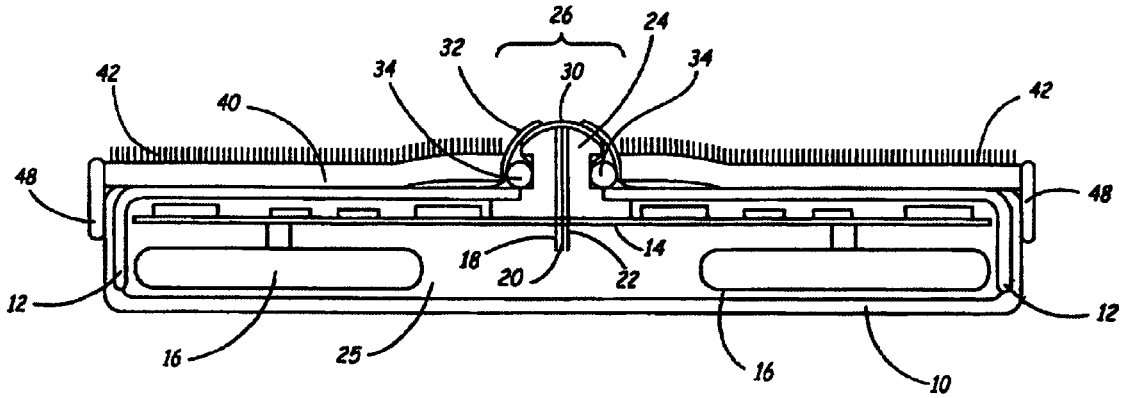

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–30 are cancelled.

* * * * *